US008672945B2

(12) United States Patent
Lavallee et al.

(10) Patent No.: US 8,672,945 B2
(45) Date of Patent: Mar. 18, 2014

(54) DEVICE FOR POSITIONING A BONE CUTTING GUIDE

(75) Inventors: Stéphane Lavallee, Saint Martin d'Uriage (FR); Fabrice Bertrand, Froges (FR); Anthony Boyer, Saint Martin d'Heres (FR); Christopher Plaskos, Grenoble (FR)

(73) Assignee: Perception Raisonnement Action en Medecine, La Tronche (FR)

( * ) Notice: Subject to any disclaimer, the term of this patent is extended or adjusted under 35 U.S.C. 154(b) by 1875 days.

(21) Appl. No.: 11/296,969

(22) Filed: Dec. 8, 2005

(65) Prior Publication Data

US 2006/0122617 A1 Jun. 8, 2006

(30) Foreign Application Priority Data

Dec. 8, 2004 (EP) .................................... 04106402

(51) Int. Cl.
*A61F 5/00* (2006.01)
(52) U.S. Cl.
USPC .............................................. 606/87; 606/88
(58) Field of Classification Search
USPC .......... 606/87, 88, 86 R, 96, 97, 98; 600/424, 600/425, 426
See application file for complete search history.

(56) References Cited

U.S. PATENT DOCUMENTS

| 5,474,559 | A | 12/1995 | Bertin et al. | |
|---|---|---|---|---|
| 5,562,674 | A | 10/1996 | Stalcup et al. | |
| 5,925,049 | A | 7/1999 | Gustilo et al. | |
| 6,193,721 | B1 * | 2/2001 | Michelson | 606/70 |
| 6,423,068 | B1 * | 7/2002 | Reisberg et al. | 606/281 |
| 6,554,837 | B1 | 4/2003 | Hauri et al. | |
| 6,711,432 | B1 * | 3/2004 | Weiss et al. | 600/427 |
| 6,712,824 | B2 | 3/2004 | Millard et al. | |
| 2002/0198531 | A1 | 12/2002 | Millard et al. | |
| 2003/0069591 | A1 * | 4/2003 | Carson et al. | 606/130 |
| 2004/0039396 | A1 * | 2/2004 | Couture et al. | 606/87 |
| 2004/0181144 | A1 | 9/2004 | Cinquin et al. | |
| 2005/0021039 | A1 * | 1/2005 | Cusick et al. | 606/88 |
| 2005/0209605 | A1 * | 9/2005 | Grimm et al. | 606/96 |
| 2006/0200161 | A1 * | 9/2006 | Plaskos et al. | 606/88 |
| 2006/0241645 | A1 | 10/2006 | Lavallee | |

FOREIGN PATENT DOCUMENTS

| EP | 1013231 | | 6/2000 |
|---|---|---|---|
| EP | 1444957 | | 8/2004 |
| FR | 2714811 | | 7/1995 |
| FR | 0307340 | A1 | 12/2004 |
| WO | 98/32384 | | 7/1998 |

* cited by examiner

*Primary Examiner* — Jan Christopher Merene
(74) *Attorney, Agent, or Firm* — Kim Winston LLP

(57) ABSTRACT

A device for positioning a cutting guide with respect to a bone comprising a body forming the cutting guide or intended to be fixed to the cutting guide; a least two contact members intended to freely contact the bone; and adjustment means for individually varying the relative position of the body with respect to each contact member.

12 Claims, 6 Drawing Sheets

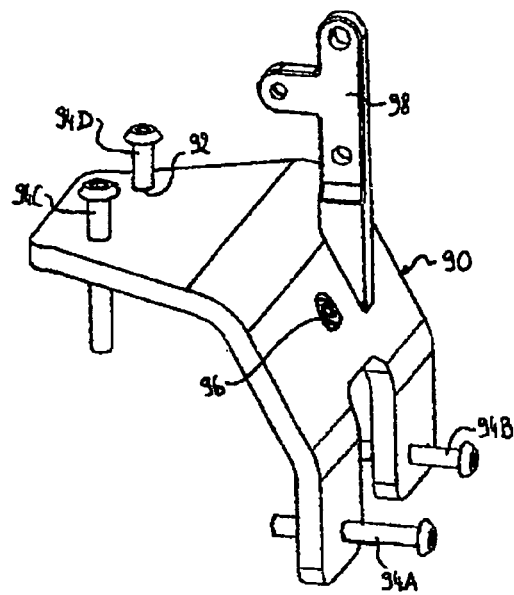
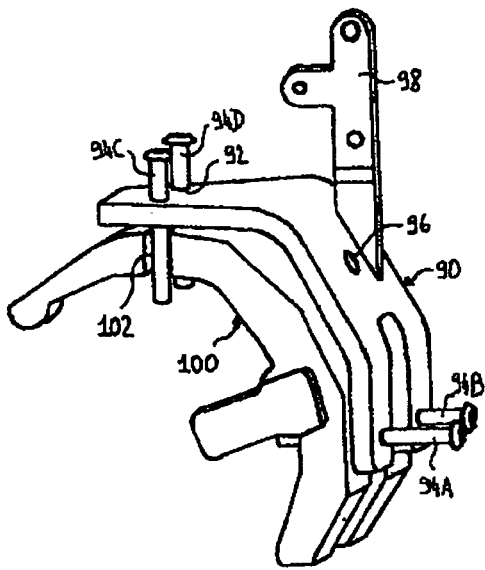
Fig.6  Fig.7
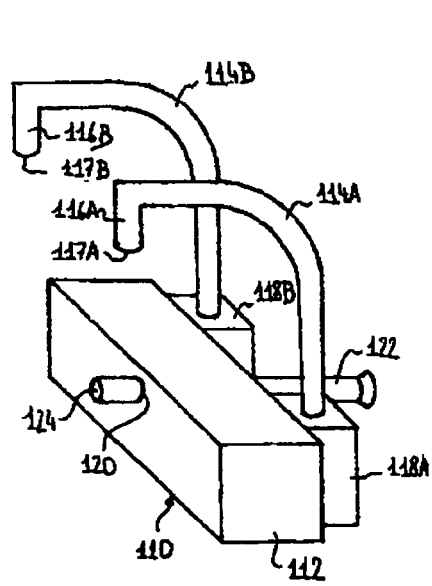
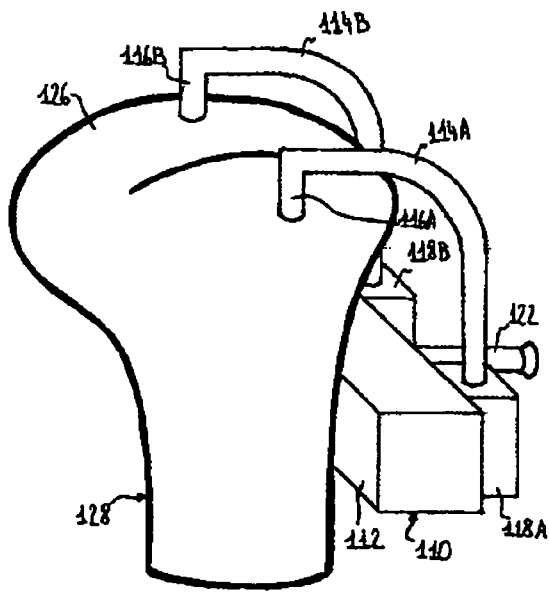
Fig.8  Fig.9

DEVICE FOR POSITIONING A BONE CUTTING GUIDE

This application claims the benefit of European Application No. 04106402,3, filed Dec. 8, 2004, the entire disclosure of which is incorporated herein by reference in its entirety.

BACKGROUND OF THE INVENTION

1. Field of the Invention

The present invention relates to a device for positioning a cutting guide relative to a bone. It applies to orthopaedic surgical procedures such as, for example, joint replacement surgery.

2. Discussion of the Related Art

In joint replacement operations, it is often required that portions of the ends of the bones of the joint be resected and replaced with endoprosthetic implants. In particular, for knee joint replacements, it is very important that the implants be well positioned on and well oriented to each bone, because deviations of 2 mm or 2° can jeopardize the success of the operation.

In order to cut the bones in a specific cutting plane, a surgeon commonly uses a cutting guide which includes a flat or slotted surface for guiding a saw blade in the cutting plane. Some cutting guides allow the guiding of the saw blade in several different cutting planes. For example, some cutting guides define 4, 5 or even 8 cutting planes and are generally called 4-in-1, 5-in-1 and 8-in-1 cutting guides, respectively. Examples of such cutting guides can be found in United States patent U.S. Pat. No. 5,474,559 filed by Zimmer and Dennis W. Burke and entitled "Femoral milling instrumentation for use in total knee arthroplasty with optional cutting guide attachment" and in patent application WO 98 32 384, filed by the New York Society for the Ruptured and Crippled Maintaining the Hospital for Special Surgery and entitled "Method and apparatus for femoral resection".

The surgeon usually positions a cutting guide relative to a bone by means of a positioning device. There exist several types of device for positioning a cutting guide relative to a bone.

United States patent U.S. Pat. No. 5,562,674, filed by Zimmer and entitled "Intramedullary rod with guide member locator" describes a device for positioning a cutting guide including a intramedullary rod with an adjustment mechanism to position the cutting guide in the correct varus/valgus orientation with respect to the intramedullary canal of the bone.

United States patent U.S. Pat. No. 6,712,824 filed by Aesculap AG & CO KG and entitled "Apparatus for positioning the angle of a bone cutting guide" describes an apparatus for positioning the cutting angle of a bone cutting guide, wherein the bone is a tibia or a femur, which includes a first fastener to fasten the positioning apparatus to the bone such that the whole of the apparatus and the fastener of the cutting guide can rotate relative to the fastening axis, and a second fastener to fasten the positioning apparatus at a second fastening location onto the bone different from the first fastening location, so as to fix the apparatus at a required position within the rotation relative to the first fastening axis.

Computer navigation has been recently introduced into surgery to aid the surgeon in positioning cutting guides accurately relative to the bones. In these devices, marking elements are attached to the bones, and their positions are monitored with a suitable camera. For example, the marking elements are passive light reflecting spheres or disks, or active infrared light or ultrasound emitters. By kinematic movements, or by scanning points on the bones, the navigation system can determine and/or display the optimal position of each implant in a coordinate system associated to the bone, as per a surgical criterion, such as alignment relative to the mechanical axis of the bones.

United States patent U.S. Pat. No. 6,554,837 filed by Plus Endoprothethik and entitled "Device and method for inserting a prosthetic knee" describes a positioning device with a base that attaches to the bone. This positioning device is actuated by motors commanded by a computer.

French patent application FR 03/07340, still not published, filed by PRAXIM and entitled "Dispositif de positionnement de guide de coupe osseuse" describes a 6 degrees of freedom cutting guide positioning device, the position of which is monitored by a localization device.

The main disadvantage of the previously described positioning devices is that they rely on an anchoring member or a base component which must be first fixed to the bone, and a number of positioning elements that connect the cutting guide to the base for adjusting the angle and/or the position of the cutting guide relative to the base with a least 1 and up to 6 degrees of freedom. These types of devices therefore usually take up considerable space in the vicinity of the bone and are invasive for the patient. Moreover, since an anchoring member or a base component is first fixed to the bone, such positioning devices lead to unnecessary damages of the bone. Besides, such positioning devices are usually time consuming to install.

SUMMARY OF THE INVENTION

The present invention aims at providing a positioning device for positioning a cutting guide relative to a bone that does not require a base element or anchor to be first fixed to the bone.

The present invention also aims at providing a positioning device that does not take up a large volume in the area of the cutting guide and the bone.

The present invention also aims at providing a positioning device that requires, to be inserted, an incision which is mostly not more invasive that the incision necessary to insert the cutting guide.

The present invention also aims at providing a positioning device that can be pre-adjusted such that when placed on the bone, the cutting guide position coincides substantially to the desired position.

The present invention also aims at providing a positioning device that can precisely adjust or fine tune the position of the cutting guide after it is placed on the bone.

To achieve all or part of these objects as well as others, the present invention provides a device for positioning a cutting guide with respect to a bone comprising a body forming the cutting guide or intended to be fixed to the cutting guide; a least two contact members intended to freely contact the bone; and adjustment means for individually varying the relative position of the body with respect to each contact member.

According to an embodiment of the present invention, each contact member is linked to the body according to a one degree of freedom connection.

According to an embodiment of the present invention, the device comprises a further contact member intended to freely contact the bone, the further contact member being fixed with respect to the body.

According to an embodiment of the present invention, at least one contact member is a screw, the tip of which being intended to freely contact the bone, the body including a threaded hole receiving the screw.

According to an embodiment of the present invention, at least one contact member includes a curved portion.

According to an embodiment of the present invention, the body includes means for guiding a cutting tool with respect to at least one cutting plane, and wherein the contact members do not cross the cutting plane.

The present invention also provides a system for assisting a surgeon in cutting portions of a bone, comprising a device for positioning a cutting guide as previously described; means for determining a theoretical position of said device relative to the bone; localization means for determining an actual position of said device relative to the bone; and means for providing data representative of the difference between the actual position and the theoretical position.

According to an embodiment of the present invention, the system comprises means for displaying an image representative of said device at the actual position, and an image representative of said device at the theoretical position.

According to an embodiment of the present invention, the system comprises means for measuring the position of each contact member relative to the body of said device.

The foregoing objects, features, and advantages of the present invention, as well as others, will be discussed in detail in the following non-limiting description of specific embodiments in connection with the accompanying drawings.

BRIEF DESCRIPTION OF THE DRAWINGS

FIG. 6 shows a third embodiment of a positioning device according to the present invention;

FIG. 7 shows the positioning device of FIG. 6 associated with a cutting guide;

FIG. 8 shows a fourth embodiment of a positioning device according to the present invention;

FIG. 9 shows the positioning device of FIG. 8 positioned on a tibia;

DETAILED DESCRIPTION

Figure 1:
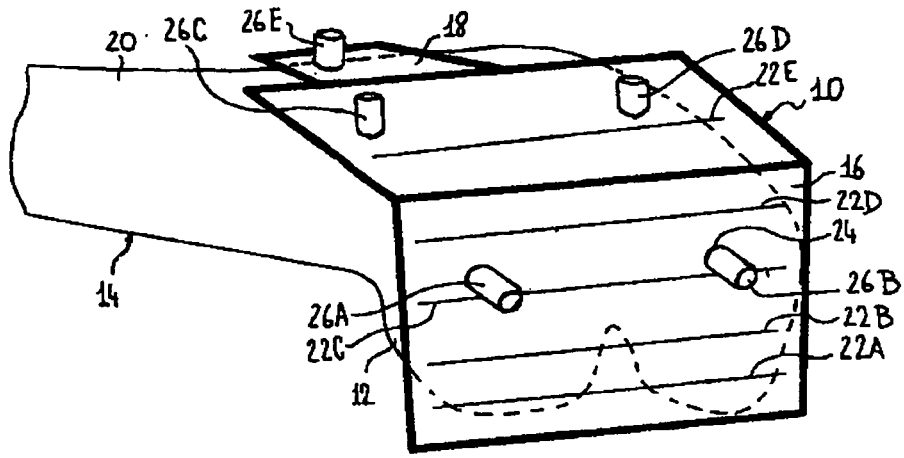
FIG. 1 very schematically shows a first embodiment of a device for positioning a cutting guide according to the present invention.

Same elements have been designated with same reference numerals in the different drawings. For clarity, only those elements which are useful to the understanding of the present invention have been shown in the drawings and will be described hereafter.

The present invention will be described hereafter in embodiments in relation with the application to knee replacement surgery.

FIG. 1 shows very schematically a cutting guide 10 positioned at the end 12 of a bone 14, the femur in the present example. The cutting guide 10 comprises a body 16 which partially covers the end 12 of the bone 14 and a portion 18 extending from the body 16 towards the diaphysis 20 of the bone 14. The cutting guide 10 includes fives slots 22A-22E for guiding a saw blade, not shown, relative to five different cutting planes. The cutting guide 10 comprises five threaded holes 24, each containing a screw 26A-26E. The tip of each screw 26A-26E forms an adjustable bone contact surface when in contact with the bone 14. The cutting guide 10 is equipped with a rigid body, not shown, which includes marking elements, for example passive light reflecting spheres or disks, or active infrared light or ultrasound emitters or active or passive magnetic elements.

Each adjustable bone contact surface is displaced axially relative to the cutting guide 10 by turning the respective screw 26A-26E. By selectively turning each screw 26A-26E, the position of the cutting guide 10 is adjusted relative to the bone 14. In the first embodiment, the screws 26A-26E are incorporated into the cutting guide 10 such that a displacement of an adjustable bone contact surface results in a displacement of the cutting guide 10 according to a direction or an angle which corresponds more or less to a clinically relevant direction or angle of the surgical operation. For example, the screws 26A and 26B are in contact with the bone 14 near the most distal portions of the condyles, the screws 26C and 26D are in contact with the bone 14 at the anterior portions of the condyles, and the screw 26E is in contact with a more proximal area of the anterior aspect of the distal femur 20 of the bone 14. With such a configuration, the screws 26A and 26B adjust mainly the distal cut and the varus/valgus angle of the cutting guide 10, the screws 26C and 26D adjust mainly the rotation and the flexum angle of the cutting guide 10 and the screw 26E adjusts mainly the anterior height of the cuts. In the first embodiment, the lateral displacement of the cutting guide 10 is performed manually. As an alternative, lateral screws are provided to adjust the lateral displacement of the cutting guide 10.

In a second embodiment of the present invention, the contact between the cutting guide and the bone is shared between at least 2 adjustable bone contact surfaces and at least one non adjustable contact surface which is integral to or rigidly fixed to the cutting guide. In this embodiment, the system provides at least one mechanical constraint to assure that the guide is positioned in a specific manner with respect to the bone. This positioning constraint preferably complies with some surgical criteria, such as, for example, preventing notching of the anterior femoral cut, or specifying a fixed cutting depth as referenced from one of the distal condyles at the end of the bone. Optionally, additional mechanical constraints can be provided to stabilize the cutting guide relative to the bone.

Figure 2:
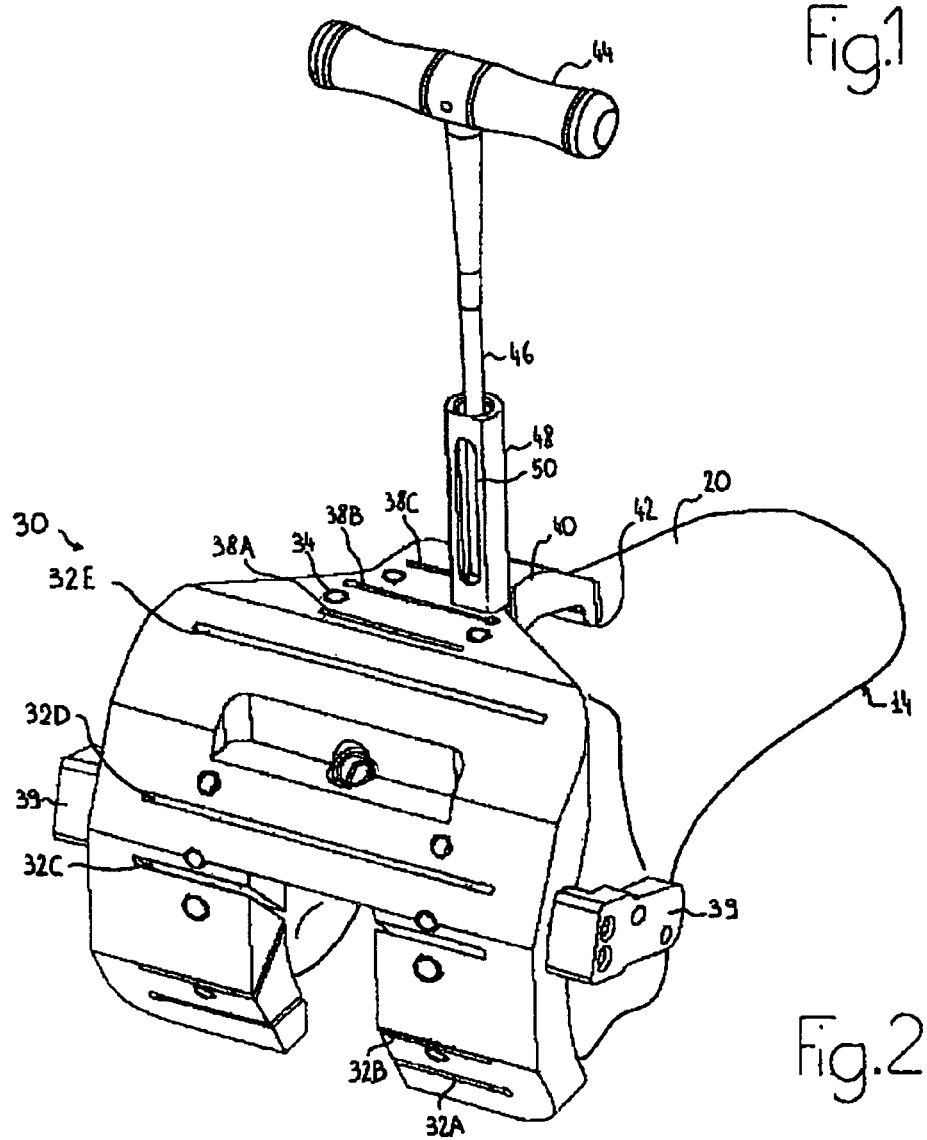
FIG. 2 shows a second embodiment of a positioning device according to the present invention.
Figure 3:
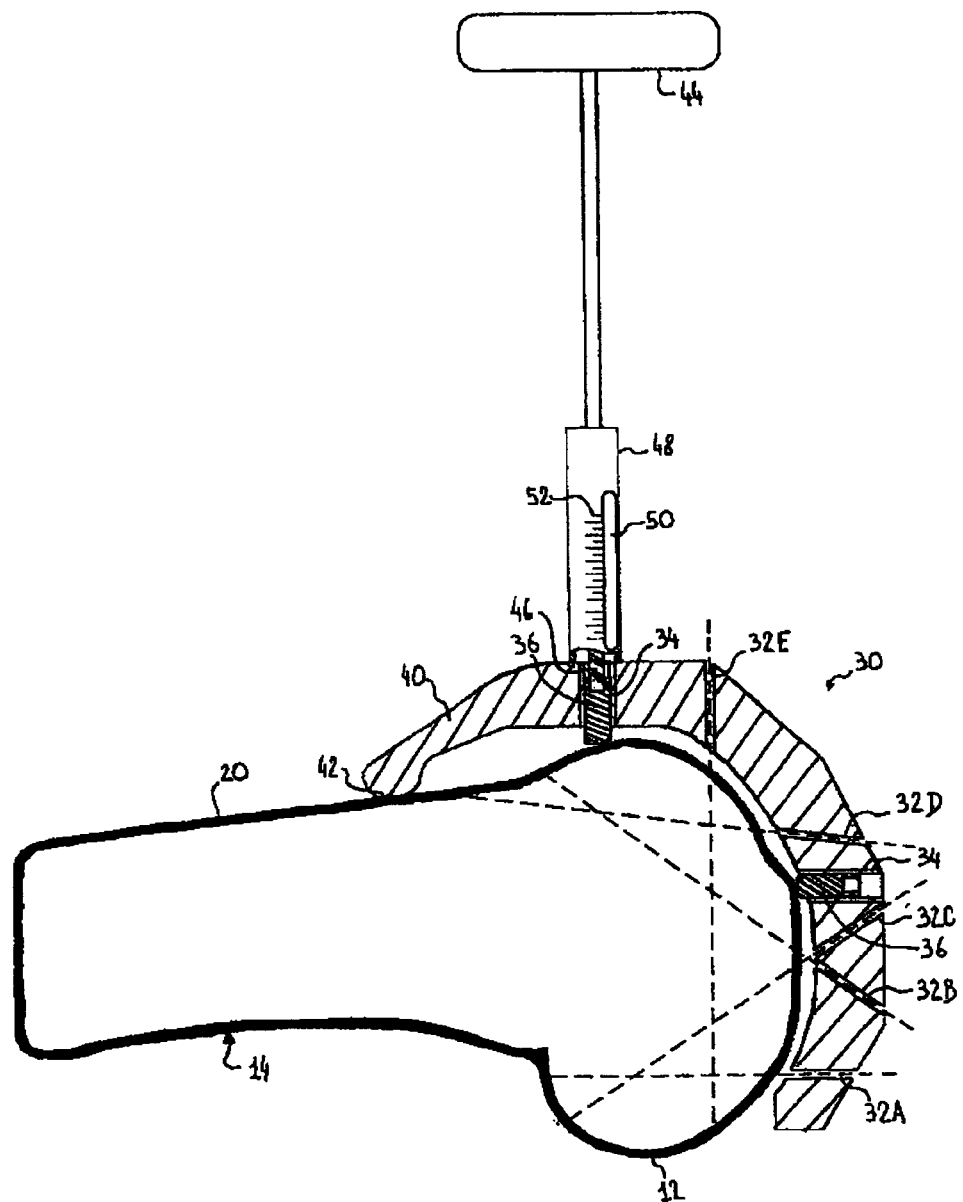
FIG. 3 is a section view of the positioning device of FIG. 2.

FIGS. 2 and 3 show an example of a cutting guide 30 according to such a second embodiment, still in relation to knee replacement surgery. In contrast with the first embodiment, the guide positioning system does not include a screw similar to screw 26E which, in the first embodiment, is in contact with the bone 14 near the diaphysis 20. Instead, it includes an extending arm 40 with an end 42 which forms a contact surface that comes into contact with the diaphysis 20 of the bone 14 and which is not adjustable relative to the cutting guide 30. In this embodiment, adjustable contact elements adjust mainly the flexion/extension angle of the cutting guide when adjusted simultaneously, and the axial rotation angle when adjusted individually. The anterior/posterior positioning of the guide is largely limited by the fixed contact point 42. It should be noted that the positions of the mechanical constraints relative to the guide are not limited to the anterior portion of the guide as shown in FIGS. 2 and 3, but can also be incorporated into the distal, posterior, lateral, or central portions of the guide to limit the position of the guide in the appropriate directions as relevant to the specific surgical technique. For example, the medeolateral positioning could be limited with a fixed mechanical constraint in the central or lateral portion of the distal aspect of the cutting guide in order to substantially center the guide with respect to the intracondular notch of the distal femur.

Optionally the cutting guide 10 can be comprised of a plurality of threaded holes 34 and at least some of these threaded holes 34 can contain a recessed screw 36, with one threaded hole being hidden under element 48 in FIG. 2. The particular combination of the threaded holes that contain a screw can be chosen based on, for example, the geometry of the bone, the level of soft tissue exposure, the degree of stability desired, or the surgeon's preference. As an alternative, more screws are added to stabilize the cutting block in all its degrees of freedom. For instance, if a total of ten screws are used, the final shape made by the tips of the screws will find a single position on the bone.

In any case, a computer system assisting the surgeon can be configured to accommodate any combination of screws, by allowing the surgeon to select, for example, on a touch screen or with a foot pedal which combination of screw holes he prefers to use. Preferably, the computer system will suggest an optimal combination of screw holes based on the geometry of the bone, or for example, on the quality of the geometrical bone model in the region of the screw holes. The quality of the bone model can be estimated, for example, using the number and the position of the digitized points, or the error between the digitized points and the "morphed" or deformed three dimensional model of the bone surface.

In FIGS. 2 and 3, the height of each screw 36 is smaller than the height of the threaded hole 34 which receives it so that each screw 36 can be maintained inside the associated hole 34 without protruding from the cutting guide 30 on the surface of the cutting guide opposite to the bone 14. The cutting guide 30 includes three further slots 38A-38C. One 30 of these slots can used to fix a rigid body with marking elements, not shown, to the cutting guide 30. The cutting guide 30 includes two opposite lateral portions 39.

Additionally, the optimal overall length of each screw can be provided by the computer system, based on a database of available screw lengths. The surgeon or assistant can then insert the corresponding screw into the appropriate hole as advised by the computer display screen. The optimal length of the screw can be calculated, based on data such as the distance along the screw axis, measured from the bone surface to the outer surface of the cutting guide, such that the screw end is not protruding out from the cutting guide outer surface, for example.

The actuation of the screws 36 for the first or the second embodiment can be aided by the use of a special screwdriver 44 having a shaft 46 with a tip corresponding to the screw heads. In FIG. 2, the screwdriver 44 shown is a manual screwdriver. Alternatively, the screwdriver 44 is an automatic screwdriver, for example an electric screwdriver, comprising an actuator, for example an electric motor, able to rotate the shaft 46. A measuring device 48 comprising a graduated cylinder can be placed on the cutting guide 30 at the threaded hole 34 containing the screw 36 to turn. The graduated cylinder 48 comprises a lateral opening 50 with graduations 52. The shaft 46 of the screwdriver 44 is introduced through the cylinder 48 and is put into contact with a screw 36. By comparing the position of a mark on the shaft 46, visible through the opening 50 of the cylinder 48, with the graduations 52 of the cylinder 48, the position of the screw head with respect to the cutting guide 30 can be determined. Optionally, the measuring device 48 can be attached directly onto the shaft 46 of the screwdriver to make it easier to handle, by for example, using a spring to push the cylinder against the outer surface of the cutting guide and a lip to retain the cylinder on the shaft. Alternatively, graduations could be engraved directly onto the shaft of the screwdriver 48 to measure the screw position, relative to, for example, the outer surface of the cutting guide. Inversely, the graduations could be incorporated into the cutting guide surfaces directly.

As shown on FIG. 3, the threaded holes 34 are located on the cutting guide 30 so that when in contact with the bone 14, the screws 36 do not cross the cutting planes. There is then no need to remove the screws 36 before making the cuts.

In the two embodiments previously described, a suitable localization device, linked to a computer, is adapted to locate the positions of the rigid body attached to the cutting guide 10, 30. The position of the bone 14 is also determined, by way of example, by means of a rigid body attached to the bone 14. The computer is linked to a display interface which can display an image representative of the cutting guide 10, 30 and an image representative of the bone 14 in their relative positions.

An example of a method for positioning the cutting guide 10, 30 according to the first or second embodiments of the present invention is now described. The first step consists in establishing a three-dimensional model of the bone. Such a three-dimensional model is obtained, for example, from palpation of some specific anatomical points of the bone and warping a three-dimensional theorical model to make it match the palped points. Another way to obtain such a three-dimensional model is to use medical image data such as those obtained from computed tomography, X-rays, MRI, fluoroscopy, ultrasound, or other modalities. The model of the bone can be very simple and can comprise only few specific anatomical points, obtained, for example, from palpation of the bone. A particular femoral knee implant is then selected, for example, on the basis of an analysis of the three-dimensional model of the bone. The computer then gives the ideal relative position of the cutting tools with respect to the bone. With the cutting guide according to the first and second embodiments previously described, only five cuts are made. In this case, the lateral position of the guide with respect to the bone needs not be defined and only five degrees of freedom are defined. With a cutting guide defining eight cutting planes, six degrees of freedom need to be determined, which means that the computer determines a unique position of the cutting guide relative to the bone.

The surgeon then positions manually the cutting guide on the bone. The computer displays the actual position of the cutting guide 10, 30 with respect to the ideal position of the cutting guide. The computer then indicates to the surgeon what should be the relative position of each screw with respect to the cutting guide 10, 30 so that the cutting guide reaches the ideal position relative to the bone. The adjustment of the screws is made by the surgeon with the screwdriver 44, for example. Alternatively, the adjustments may be made by hand if longer screws with larger heads are used. The computer indicates, for example, how far each screw needs to be screwed, or how many revolutions it needs to be turned to bring the guide to the desired position, or both. This can be done, for example, by tracking the bone position and the actual guide position, and by calculating the difference between the distance from the bone surface to (a) the desired guide position, and to (b) the actual guide position, along the direction of each screw axis. Alternatively, when an automatic screwdriver is used, the screwdriver can be controlled by the computer. The surgeon then places, successively for each screw to be actuated, the screwdriver so that it cooperates with the screw and the computer controls the screwdriver to displace the screw so that the cutting guide reaches the ideal position relative to the bone.

Figure 4:
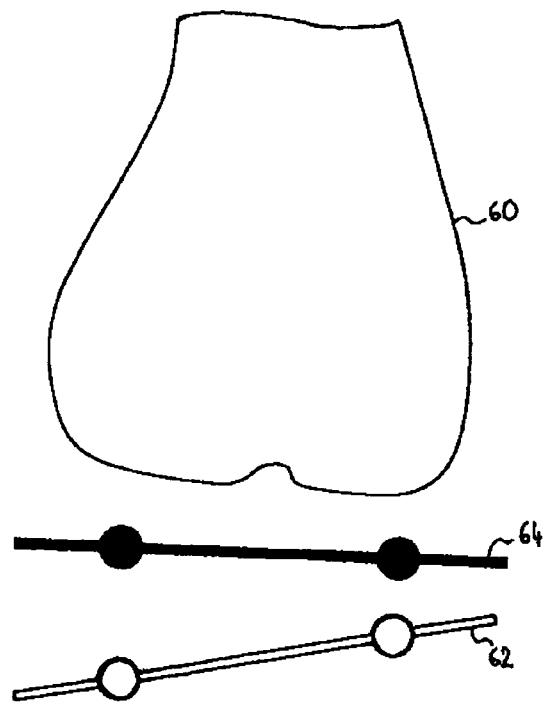
FIG. 4 very schematically shows an example of a display on a display apparatus for assisting the positioning of the cutting guide.

FIG. 4 shows an example of display suitable for the first or second embodiment. The display shows a schematic section view of the bone and the cutting guide in a plane containing two adjacent screws, for example the screws 26A and 26B on FIG. 1. It includes a schematic image 60 representing the bone 14, a schematic image 62 representing the cutting guide, with the two screws, at the actual position of the cutting guide and a schematic image 64 representing the cutting guide, with the two screws, at the ideal position of the cutting guide. The display also indicates the adjustments to be made for the two screws. A similar display can be shown for the screws 26C and 26D. The display can also change the colour of the screws to indicate, for example, which of the screws needs to be adjusted the most to bring the guide to the ideal position. Optionally, the display can also show lines representing various edges or midlines of the ideal and the actual cutting guide positions, so as to aid, for example, medial/lateral positioning. Alternatively, the display can show semi-transparent three-dimensional models of the ideal and the actual cutting guide positions. In the particular case of the cutting guide 30 according to the second embodiment of the present invention, the end 42 of the extending arm 40 forms a contact surface that comes into contact with the diaphysis 20 of the bone 14 and which is not adjustable relative to the cutting guide 30. The system then integrates this constraint and reduces the number of degrees of freedom for changing the position of the cutting guide 30 with respect to the three-dimensional model of the bone 14. Namely, the antero-posterior of the cutting guide 30 is constrained such that the end 42 of the extending arm 40 stays on the bone surface. Preferably, the screws are located on the cutting guide so that, when the cutting guide is positioned relative to the bone, they lie on a surface of the bone which is expected to be more or less flat so that any adjustment of a screw tends not to affect too much the position of the contact surfaces of the others screws. The display of the desired and actual guide positions, and of the bones, can be aided with the use of semitransparent three dimensional models.

Once the ideal position of the cutting guide is achieved, the cutting guide is fixed to the bone, for example, by means of pins or screws, and the cuts are then made. For example, when the cutting guide is positioned, the surgeon uses one hand to fix a pin located close to the location of the screw 26E for the cutting guide 10 according to the first embodiment of the invention or close to the end 42 of the extending arm 40 of the cutting guide 30 according to the second embodiment of the invention, while he holds the cutting guide in the other hand. Alternatively, fixation screws or pins can also be provided at the lateral portions 39.

In a preferred embodiment of the invention, the adjustment of the screws is made away form the operation region, during preparation of the cutting guide just before it is positioned on the bone. For each screw, the system computes a nominal value of distance so that the screw will come into contact with the three-dimensional model of the bone. Each screw is then positioned to its nominal value, for example, by means of the screwdriver 44 and the graduated cylinder 48. Once the nominal values have been pre-set for each screw, the surgeon positions the cutting guide on the bone. Final adjustments are performed on each screw if necessary to compensate for small errors of initial screw pre-setting, the three-dimensional model and the localization device accuracy.

Figure 5:
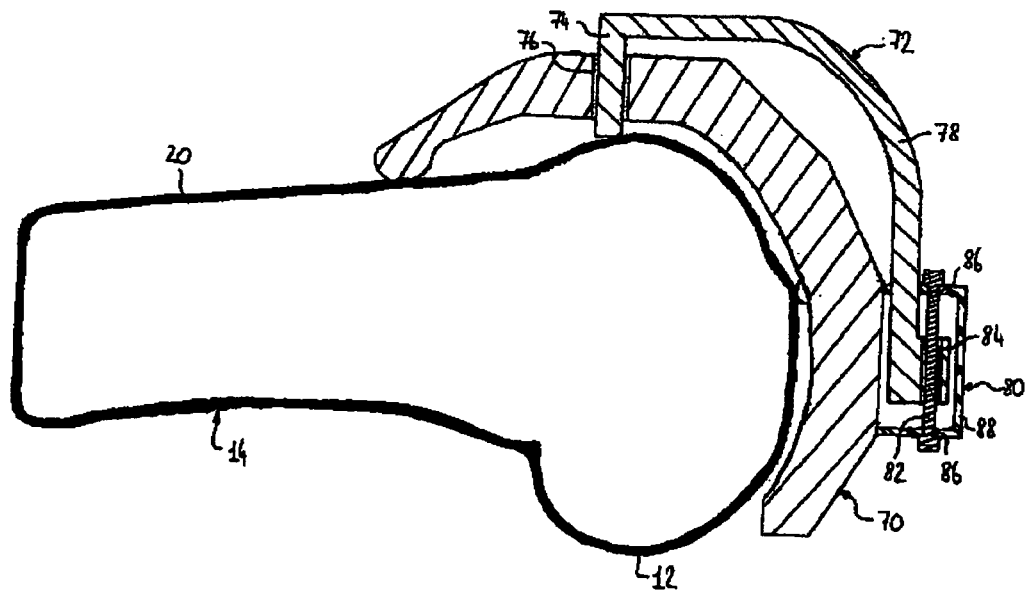
FIG. 5 is a section view of an alternative of the positioning device of FIG. 2.

FIG. 5 shows a similar section view as FIG. 3 of an alternative cutting guide 70. In such an alternative, at least one bone contact surface does not directly correspond to the tip of a screw but corresponds to the tip of an intermediate element 72 which includes a portion 74 that passes adjacent to the cutting guide 70. Alternatively, portion 74 can be cylindrical and can pass through a hole 76 provided in the cutting guide. The cylinder portion 74 is linked, by a curved arm 78, to an actuation mechanism 80 including a driving worm 82 cooperating with a threaded hole 84 provided at an end of the curved arm 78. The driving worm 82 is mounted at its opposite ends into bearings 86 of a case 88 attached to the cutting guide 70. The actuation of the driving worm 82, is for example, made by use of the screwdriver 44 of FIG. 2. The axis of the driving worm 82 is parallel to the axis of the cylinder portion 74 so that the actuation of the driving worm 82 leads to the displacement of the cylinder portion 74 along its axis. Alternatively, the intermediate member can be positioned by rotational joints instead of translational joints. This can be accomplished by incorporating an axis, for example, perpendicular to the section plane of FIG. 5, with which the intermediate member can rotate relative to the guide with. A screw positioned at some distance from this axis could then be used to push or to pull the intermediate member relative to the cutting guide, causing it to rotate about the axis. Thus a small rotation about an axis positioned in the vicinity of mechanism 80 would cause a relatively large displacement of the bone contact surface member, in a direction tangential to the said axis. Such an alternative is preferable for less invasive surgery procedures in which the access to the contact point region on the bone surface may be limited by adjacent structures such as bones or soft tissues, and in which the screw head is difficult to access. In such a case, the positioning system can be made to have a low-profile shape so that it can be slipped under the soft tissues near the cutting areas (for example, the under quadriceps muscle).

A third embodiment of the present invention will now be described wherein at least some of the adjustment screws are attached to an intermediate member which is temporarily fixed to the cutting guide.

FIG. 6 shows such an intermediate member 90 which comprises four threaded holes 92 receiving four screws 94A-94D. This intermediate member 90 is adapted to cooperate with a cutting guide, not shown on FIG. 6, having the general shape illustrated on FIG. 1 or 2. The intermediate member 90 includes a hole 96 to be located opposite to a threaded hole of the cutting guide in order to fix the intermediate member 90 to the cutting guide by use of a screw. As an alternative, the intermediate member comprises a quick release clip cooperating with a corresponding clip provided on the cutting guide so that the intermediate member can be quickly removed after the cutting guide is positioned and fixed to the bone. The intermediate member 90 includes an extending portion 98 for attaching a rigid body, not shown, with markers. As an alternative, the intermediate member includes a slot which allows a quick attachment and removal of a rigid body with markers.

FIG. 7 shows the intermediate member 90 of FIG. 6 attached to a cutting guide 100 having the general shape of the cutting guide 30 of FIG. 2. The adjustments screws 94A-94B come into contact with the bone, not shown, through openings 102 and holes provided in the cutting guide 100. As an alternative, the adjustment screws are located on the intermediate member 90 so that they pass adjacent to the cutting guide. The positioning of the cutting guide 100 equipped with the intermediate member 90 is achieved with the positioning method previously described in relation with the first or second embodiments.

Similarly, the curved elements 72 and their described positioning mechanisms (translational or rotational), described for example in relation to FIG. 5, could also be incorporated into the intermediate element 90, instead of, or in combination with, simple threaded holes 94. This allows the positioning system to be more easily integrated into the various shapes and sizes of available cutting guides as used in knee surgery, or hip surgery, or ankle surgery, or long bone surgery, etc. This also allows for the bone contacting elements and associated members to be easily removed from the cutting guide so as to facilitate access during the cutting phase. This also allows for the intermediate member 90 to be smaller and to attach only in the area of the mechanism 80, for example, to minimise the exposure required to introduce the positioning system.

FIG. 8 shows a fourth embodiment of a cutting guide 110 aimed to be positioned at the end of a tibia or a femur, for making a single cut such as the proximal tibial cut or the distal femoral cut. Such a cutting guide comprises a parallelepiped body 112 which includes at least one cutting surface or slot, not shown, for the realization of at least the single cut. The cutting guide 110 includes two curved arms 114A, 114B. A curved arm 114A, 114B continues with a cylindrical portion 116A, 116B of parallel axis, the tip of which corresponds to a contact surface 117A, 117B. The displacement of an arm 114A, 114B along the direction of the axis of the cylindrical portion 116A, 116B is obtained by means of an actuation mechanism 118A, 118B similar to the translational and rotational actuation mechanisms previously described above. The cutting guide 110 also includes a threaded hole 120 receiving a screw 122 the tip of which corresponds to a contact surface 124. The actuation of the screw 122 and the actuation mechanisms 118A, 118B is made, for example, made by use of the screwdriver 44 of FIG. 2. A rigid body, not shown, with markers is linked to the body 112.

FIG. 9 shows the cutting guide 110 of FIG. 8 positioned on the end 126 of a tibia 128. The actuation of the actuation mechanisms 118A, 118B adjust mainly the cut height, when actuated simultaneously, and the varus/valgus angle of the cutting guide 110 when actuated separately. The actuation of the screw 122 adjusts mainly the flexum angle of the cutting guide 110. As an alternative, the cutting guide 110 comprises an extending portion, not shown, from the body, the end of which is maintained in contact on the anterior aspect of the tibia for stability. This extending portion can be made to better conform to the shape of the bone surface, be for example using curved surfaces. The positioning of the cutting guide 110 according to the fourth embodiment of the invention is achieved with the positioning method previously described in relation with the first or second embodiments.

Figure 10:
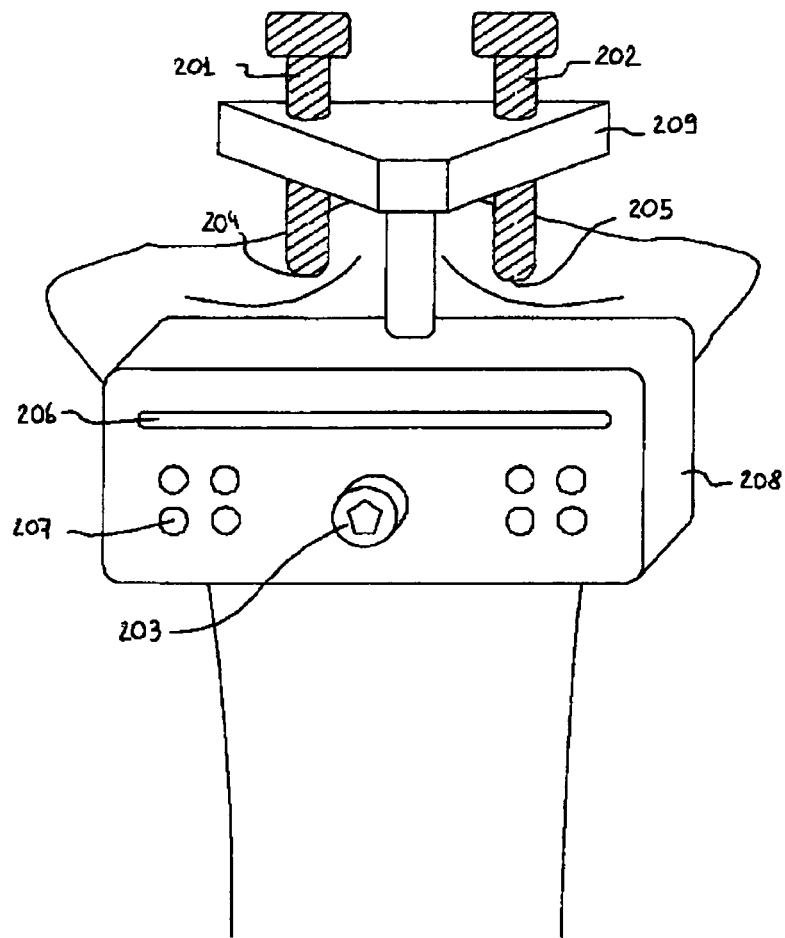
FIG. 10 shows a fifth embodiment of a positioning device according to the present invention.

FIG. 10 very schematically shows a fifth embodiment of a cutting guide for making a single cut on the tibia or femur in which the screw tips are directly used as the bone contact surfaces. Shown in FIG. 10 are the cutting block 208, cutting slot 206, fixation pin or screw holes 207, and a triangular shaped member 209 which contains threaded holes for screws 201 and 202 with corresponding contact surface elements 204 and 205, and a third screw 203 with a contact surface element 213, not visible on FIG. 10. Screw 203 is arranged so that it is substantially perpendicular to screws 201 and 202. This particular embodiment works under the same principles as those described above, though the system has the advantage of being simpler to design and manufacture with less moving parts. Additionally, the cut can be made through the cutting slot without having to remove any screws or detach any intermediate parts to make the cuts.

The adjustment systems described in the FIGS. 8-10 can be made detachable from the cutting guide as described in the third embodiment. Adjustment of the three screws 201, 202, and 203, in this system cause the same motions as those described in the fourth embodiment.

A disadvantage of the invention as disclosed above is that in some cases the surgeon must displace two bone contact elements by the same distance (i.e. equally, or "simultaneously") to achieve a linear displacement of the guide relative to the bone, such as a change in the cutting depth, for example. This disadvantage is avoided in the sixth embodiment of the invention, as described below.

Figure 11:
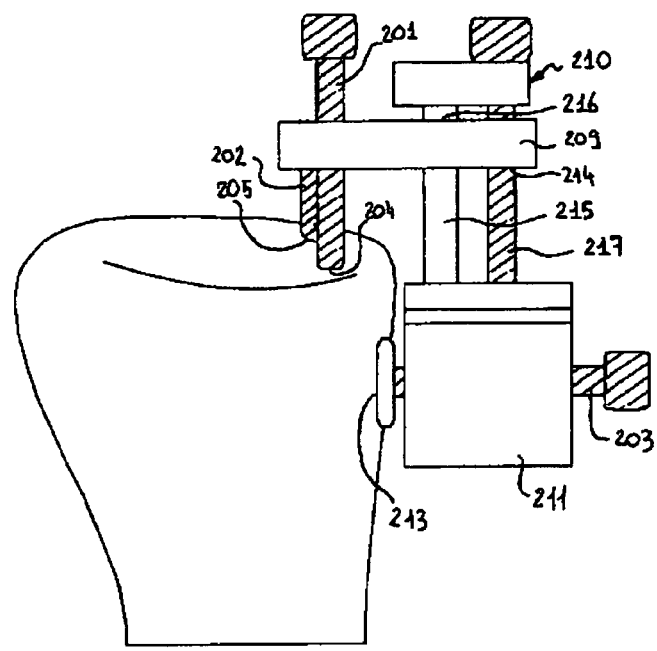
FIG. 11 shows a sixth embodiment of a positioning device according to the present invention.

FIG. 11 very schematically shows an example of the sixth embodiment of the present invention which is an alternative of the fifth embodiment shown in FIG. 10. In this embodiment, the position of at least two of the adjustable contact surfaces can be adjusted with a single adjustment mechanism. Screw 202 in FIG. 10 has been replaced by a fixed member in FIG. 11. In this embodiment, the triangular shaped member 209 can be displaced with respect to rest of the cutting guide by means of a mechanism 210. Similar to actuation mechanism 80, actuation mechanism 210 can be comprised of a driving worm 217, mounted at its opposite ends with bearings, cooperating with a threaded hole 214 provided a the triangular shaped member 209. A linear guide 215, such as a cylinder extending from the guide and cooperating with a hole 216 in the triangular shaped member 209, for example, could be used to guide the motion. Alternately, a dove tail joint or similar linear joint could be used to guide the motion. Alternately, a rotational mechanism could be employed such as the alternate rotational mechanism described above for actuation mechanism 80. The bone contact elements 205 and 204 are simultaneously adjusted relative to the cutting guide when the mechanism 210 is actuated. Turning screw 201 displaces only contact element 204 relative to the cutting guide, and turning screw 203 displaces only contact element 213 relative to the cutting guide. Thus actuating the mechanism 210 causes mainly a change in cutting depth, and turning the screw 204 causes a change in varus/valgus angle. This embodiment has the advantage of decoupled motions and is thus easier and more intuitive to use.

This principle as described in the fifth embodiment can be extended to the other embodiments of the invention. In FIG. 1, for example, the screws 26A and 26B could be arranged in the same manner as described in FIG. 11, such that when screw 210 is turned, both screws 26A and 26B move equally relative to the cutting guide causing a change in distal cutting depth only. Similarly, this mechanism could be applied to the screws 26D and 26C to obtain the same results.

Additionally, this arrangement can be made to detach from the cutting guide as in the third embodiment.

In the embodiments previously described, the tips of the screws or cylindrical portions which form contact surfaces are spherical in order to be placed easily on any surface. As a further alternative, the tips have a small flat surface. As a further alternative, the tips have a curved surface that is the negative part of the bone surface usually expected in such anatomical area. The choice of the shape of the tip can depend on the local shape of the bone surface in the area of the screw tip. Sharp tips can also be used to optimise the stability of the guide during positioning and fastening. For instance, in some cases it is advantageous to use a pointed surface for the bone contact element so that the guide does not slide around on the bone. This could also help stabilise the guide during the insertion of pins or screws before making the cut. As another alternative, the tips can be fixed or pivoting around a ball and socket joint.

In FIG. 11, for example, screw 203 has a "disc" shaped tip 213 so as to avoid instability due to the sharp ridge in the area of the anterior tibial tuberosity. This assures that the disc surface is always substantially on the ridge of the crest, on not sliding around on either side. This disc shaped tip 213 could also be made to contain a convex shaped surface (eg such as a "U" or "V" shape), and to attach to the screw 203 with a rotational or ball-and-socket joint or so as to better conform to the bone surface. For any tip shape, the tip surface can be on a ball and socket joint with respect to the screw axis so that the surface of the bone contact element can rest tangential to the bone surface. Alternatively, for any tip shape, the tip surface can be on a rotational joint with respect to the screw axis so that the bone contact element surface does not rotate on the bone surface when the screw is turned.

The above descriptions should not limit the spirit of the invention to for example the type of bone cutting guide to be positioned. This invention could be naturally extend to position, for example, a robotic cutting guide which can be used to make any type of cuts, such as planar, spherical, etc. In addition, use of the above invention is not intended to be limited to knee joint procedures, as this invention could be applied to the positioning of cutting guides for ankle surgery, knee surgery, hip surgery, shoulder surgery, elbow surgery, high tibial osteotomy surgery, etc. . . .

An advantage of the present invention is that it enables the positioning of a cutting guide on a bone without first requiring the fixing of the cutting guide to the bone.

An advantage of the present invention is that it does not take up a large volume in the area of the cutting guide and the bone.

Another advantage of first and second embodiments of the present invention is that the parts used to position the cutting guide do not have to be removed before making the cuts with the cutting guide.

The present invention has been described hereabove in relation with the knee replacement surgery. However, it may be extended to any joint replacement surgery requiring the positioning of a cutting guide.

Of course, the present invention is likely to have various alterations, modifications, and improvements which will readily occur to those skilled in the art. In particular, the slots used to guide a saw blade can be replaced by grooves for bearing the axis of a drilling machine.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

The invention claimed is:

1. A method for positioning a bone cutting guide relative to a bone, comprising the steps of:
   providing a cutting guide having at least two contact members intended for contacting the bone surface, wherein at least one of said at least two contact members is adjustably positionable relative to the cutting guide along an axis extending outwardly from the cutting guide so to permit a distance from a distal end of the contact member to the cutting guide, that defines a length of the contact member, to be adjustable and to permit the contact member to be fixed to the cutting guide in different positions along the axis resulting in the contact member having a variable fixed length;
   determining a theoretical position of said cutting guide with respect to a three-dimensional model of the bone;
   determining on the three-dimensional model of the bone the areas or points of contact at which the contact members will contact the bone when the cutting guide is positioned at the theoretical position;
   determining an adjustment value for a displacement of at least one of the contact members from the cutting guide such that when the contact member comes in contact with the bone, the position of the cutting guide corresponds to the theoretical position;
   displacing the at least one contact member from the cutting guide according to the determined adjustment value before the cutting guide is applied to the bone; and
   applying the cutting guide on the bone.

2. The method of claim 1, further comprising after said adjusting step,
   positioning the cutting guide with respect to the bone at the theoretical position to determine an actual position of said cutting guide relative to the bone;
   providing data representative of the difference between the actual position and the theoretical position; and
   fine tuning the position of the cutting guide after the cutting guide is placed on the bone using the difference data.

3. The method of claim 2, wherein, after the step of positioning the cutting guide, the relative position of the body of the device with respect to at least a contact member is varied to compensate positioning errors.

4. The method of claim 2, wherein the cutting guide is fixed to the bone after the fine tuning of the cutting guide with respect to the bone is complete.

5. The method of claim 1, wherein at least one contact member of the device is a screw, the tip of which being intended to freely contact the bone, the body including a threaded hole receiving the screw, the screw being positioned to the associated adjustment value by means of a screwdriver.

6. The method of claim 1, wherein the bone is the femur.

7. A method for positioning a bone cutting guide relative to a bone, comprising the steps of:
   providing a cutting guide having at least two contact members intended for contacting the bone surface along a contact surface, wherein at least one of said at least two contact members is adjustably positionable relative to the cutting guide along an axis that intersects the cutting guide while the contact member remains in contact with the cutting guide to permit the contact member to be fixed to the cutting guide in different positions along the axis, wherein adjustment of the contact member along the axis adjusts the length of the contact member extending outwardly from the cutting guide, thereby varying a distance between the cutting guide and the bone surface;
   determining a theoretical position of said cutting guide with respect to a three-dimensional model of the bone;
   determining on the three-dimensional model of the bone the areas or points of contact at which the contact members will contact the bone when the cutting guide is positioned at the theoretical position;
   determining an adjustment value for a displacement of at least one of the contact members from the cutting guide such that when the contact member comes into contact with the bone, the position of the cutting guide corresponds to the theoretical position;
   displacing the at least one contact member from the cutting guide according to the determined adjustment value before the cutting guide is applied to the bone; and
   positioning the cutting guide on the bone.

8. The method of claim 7, wherein the at least two contact member is rotatably adjustable relative to the cutting guide.

9. The method of claim 7, further including the steps of:
   displaying the adjustment value on a display; and changing a color of the at least one of the contact members depicted on the display to indicate which contact member needs to be adjusted.

10. A method for positioning a bone cutting guide relative to a bone, comprising the steps of:
- providing a cutting guide having at least two contact members intended for contacting the bone surface along a contact surface, wherein at least one of said at least two contact members is axially positionable relative to the cutting guide to permit a length of the contact member relative to the cutting guide to be changed and permit the cutting guide to be fixed in different positions along the axis;
- determining a theoretical position of said cutting guide with respect to a three-dimensional model of the bone;
- determining on the three-dimensional model of the bone the areas of points of contact at which the contact members will contact the bone when the cutting guide is positioned at the theoretical position;
- determining an adjustment value for a displacement of at least one of the contact members from the cutting guide so that the contact member comes into contact with the model of the bone when the cutting guide is in the theoretical position;
- displacing the at least one contact member from the cutting guide according to the determined adjustment value before the cutting guide is applied to the bone;
- determining an actual position of the cutting guide relative to the bone using a localization means; and
- displaying data representative of the difference between the actual position and the theoretical position.

11. The method of claim 10, wherein the at least two contact member is rotatably adjustable relative to the cutting guide.

12. The method of claim 10, further including the steps of:
- displaying the adjustment value on a display; and
- changing, on the display, a color of the at least one of the contact members to indicate which contact member needs to be adjusted.

* * * * *